(12) United States Patent
Green

(10) Patent No.: US 11,788,125 B2
(45) Date of Patent: *Oct. 17, 2023

(54) MOLECULAR FUSES FOR REAL-TIME, LABEL-FREE, MULTIPLEXED IMAGING OF RNAS IN LIVING CELLS

(71) Applicant: ARIZONA BOARD OF REGENTS ON BEHALF OF ARIZONA STATE UNIVERSITY, Scottsdale, AZ (US)

(72) Inventor: Alexander Green, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 213 days.

This patent is subject to a terminal disclaimer.

(21) Appl. No.: 17/324,944

(22) Filed: May 19, 2021

(65) Prior Publication Data

US 2021/0348222 A1    Nov. 11, 2021

Related U.S. Application Data

(63) Continuation of application No. 16/468,846, filed as application No. PCT/US2017/066684 on Dec. 15, 2017, now Pat. No. 11,047,000.

(60) Provisional application No. 62/434,914, filed on Dec. 15, 2016.

(51) Int. Cl.
*C07H 21/02* (2006.01)
*C12Q 1/6841* (2018.01)
*C12N 15/115* (2010.01)
*G01N 33/53* (2006.01)

(52) U.S. Cl.
CPC .......... *C12Q 1/6841* (2013.01); *C12N 15/115* (2013.01); *G01N 33/5308* (2013.01); *C12N 2310/16* (2013.01); *C12N 2310/531* (2013.01); *C12Q 2525/205* (2013.01); *C12Q 2525/301* (2013.01)

(58) Field of Classification Search
CPC ........................ C12N 15/115; C12N 2310/16
See application file for complete search history.

(56) References Cited

U.S. PATENT DOCUMENTS

| | | |
|---|---|---|
| 2015/0141282 A1 | 5/2015 | Jaffrey |
| 2019/0071737 A1 | 3/2019 | Green |
| 2019/0185856 A1 | 6/2019 | Green |
| 2019/0218624 A1 | 7/2019 | Green |
| 2019/0256898 A1 | 8/2019 | Green |
| 2019/0276901 A1 | 9/2019 | Green |
| 2019/0285620 A1 | 9/2019 | Green |
| 2019/0382746 A1 | 12/2019 | Green |
| 2020/0071777 A1 | 3/2020 | Green |
| 2020/0080137 A1 | 3/2020 | Green |
| 2020/0386750 A1 | 12/2020 | Green |
| 2021/0292772 A1 | 9/2021 | Green |

FOREIGN PATENT DOCUMENTS

| | | |
|---|---|---|
| WO | 2017147585 A1 | 8/2017 |
| WO | 2017205668 A1 | 11/2017 |
| WO | 2018026762 A1 | 2/2018 |
| WO | 2018026765 A1 | 2/2018 |
| WO | 2018027177 A1 | 2/2018 |
| WO | 2018075502 A1 | 4/2018 |
| WO | 2018093898 A1 | 5/2018 |
| WO | 2018187687 A1 | 10/2018 |

OTHER PUBLICATIONS

Arora, A., et al. (2015). Dual-colour imaging of RNAs using quencher- and fluorophore-binding aptamers. Nucleic Acids Research.
Babendure, JR et al. "Aptamers switch on fluorescence of triphenylmethane dyes." Journal of the American Chemical Society 125.48 (2003): 14716-14717.
Choi, H. M. T., et al. (2010). Programmable in situ amplification for multiplexed imaging of mRNA expression. Nature Biotechnology, 28(11), 1208-1212.
Filonov, G. S., et al. (2014). Broccoli: Rapid Selection of an RNA Mimic of Green Fluorescent Protein by Fluorescence-Based Selection and Directed Evolution. Journal of the American Chemical Society, 136(46), 16299-16308.
Green, A. A., et al. "Complex cellular logic computation using ribocomputing devices." Nature 548.7665 (2017): 117.
Green, et al., Toehold Switches: De-Novo-Designed Regulators of Gene Expression, Cell, 2014, 159:925-939.
Hoppe, et al., Single-Cell Technologies Sharpen Up Mammalian Stem Cell Research, Nature Cell Biology, 2014, 16 (10):919-927.
Lin, C., et al. (2012). Submicrometre geometrically encoded fluorescent barcodes self-assembled from DNA. Nat. Chem., 4(10), 832-839.
Mhlanga, et al., tRNA-Linked Molecular Beacons for Imaging mRNAs in the Cytoplasm of Living Cells, Nucleic Acids Research, 2005, 33(6):1902-1912.
Paige, et al., RNA Mimics of Green Fluorescent Protein, Science, 2011, 333:642-646.
Pardee, K. et al. (2016). Rapid, Low-Cost Detection of Zika Virus Using Programmable Biomolecular Components. Cell, 165(5), 1255-1266.
Pardee, K., et al. (2014). Paper-Based Synthetic Gene Networks. Cell, 159(4), 940-954.

(Continued)

Primary Examiner — Amy H Bowman
(74) Attorney, Agent, or Firm — Quarles & Brady, LLP

(57) ABSTRACT

Provided herein are imaging probes and systems and methods employing such imaging probes for real-time, label-free, multiplexed imaging of RNAs in living cells. More particularly, aptamer-based sensors ("aptasensors") and molecular fuses comprising multiple aptasensors are genetically encoded imaging probes comprising RNA-target binding sequence and an intramolecular reconfiguration sequence. The probe is configured such that binding of a RNA target by the RNA-target binding sequence triggers the intramolecular reconfiguration sequence to reconfigure such that an optically detectable output is generated by the probe.

15 Claims, 9 Drawing Sheets

Specification includes a Sequence Listing.

(56) References Cited

OTHER PUBLICATIONS

PCT International Search Report and Written Opinion, PCT/US2017/66684, dated May 4, 2018, 15 pages.
Ponchon et al. (Nature Methods, 2007, 4, 7, pp. 571-576).
Santangelo, Molecular Beacons and Related Probes for Intracellular RNA Imaging, Wiley Interdisciplinary Reviews: Nanomedicine and Nanobiotechnology, 2010, 2(1):11-19.
Sato, S., et al. (2015). Live-Cell Imaging of Endogenous mRNAs with a Small Molecule. Angew. Chem. Int. Ed., 54 (6), 1855-1858.
Shearer, R. F. et al. (2015). Experimental design for stable genetic manipulation in mammalian cell lines: lentivirus and alternatives. Genes to cells : devoted to molecular & cellular mechanisms, 20(1), 1-10.
Song, W., et al. "Imaging RNA polymerase III transcription using a photostable RNA-fluorophore complex." Nature chemical biology 13.11 (2017): 1187.
Song, W., et al. "Plug-and-play fluorophores extend the spectral properties of Spinach." Journal of the American Chemical Society 136.4 (2014): 1198-1201.
Strack, R.L. et al., "A superfolding Spinach2 reveals the dynamic nature of trinucleotide repeat-containing RNA." Nature methods 10.12 (2013): 1219.
Yin, P., et al. (2008). Programming biomolecular self-assembly pathways. Nature, 451(7176), 318-322.

MOLECULAR FUSES FOR REAL-TIME, LABEL-FREE, MULTIPLEXED IMAGING OF RNAS IN LIVING CELLS

CROSS-REFERENCE TO RELATED APPLICATIONS

This application is a continuation of U.S. patent application Ser, No. 16/468,846, filed Jun. 12, 2019, which application is a national stage filing under 35 U.S.C. § 371 of International Application No. PCT/US2017/066684, filed Dec. 15, 2017, which claims priority to U.S. Provisional Patent Application No. 62/434,914, filed Dec. 15, 2016, the entirety of each are incorporated herein by reference.

STATEMENT REGARDING FEDERALLY FUNDED RESEARCH OR DEVELOPMENT

This invention was made with government support under GM126892 awarded by the National Institutes of Health. The government has certain rights in the invention.

REFERENCE TO A SEQUENCE LISTING SUBMITTED VIA EFS-WEB

The content of the ASCII text file of the sequence listing named "112624_00942_seqlist_txt.TXT" which is 2.30 kb in size was created on May 19, 2021, and electronically submitted via EFS-Web with the application is incorporated herein by reference in its entirety.

BACKGROUND

The development of GFP and other genetically encoded fluorescent proteins revolutionized the study of cell biology, enabling scientists to directly visualize gene expression and the organization of proteins inside living cells in a straightforward and minimally perturbative fashion.

Over the years, an array of innovative technologies for imaging RNA expression and localization in living cells has also been developed. These methodologies fall into two general categories. The first encompasses imaging probes produced using synthetic chemistry, such as so-called molecular beacons and smart-flares. These probes enable multiplexed RNA imaging by interacting directly with targeted RNAs through Watson-Crick base pairing; yet, they must be introduced into the cell from outside using potentially harsh and/or inefficient delivery methods.

The second category encompasses genetically encoded probes, such as MS2-GFP fusions and the spinach RNA aptamer, which can be transiently or stably expressed within cells and thus avoid challenges of delivery. These genetically encoded approaches, however, are implemented by strongly perturbing the target RNA, adding aptamers to its sequence, which can interfere with native RNA processing. Furthermore, these genetically encoded systems have limited multiplexing capacity and suffer from high background or weak output signals.

SUMMARY

This disclosure is related to imaging of RNA in living cells without the use of labels. More particularly, the embodiments provided herein relate to an innovative set of genetically encoded imaging probes termed molecular fuses that for the first time provide label-free, highly multiplexed, real-time RNA imaging in live cells.

In a first embodiment, provided herein is an aptasensor imaging probe comprising a ribonucleic acid (RNA) polynucleotide comprising an RNA-target binding sequence and an intramolecular reconfiguration sequence, said probe configured such that binding of a RNA target by said RNA-target binding sequence triggers said intramolecular reconfiguration sequence to form an active aptamer such that an optically detectable output is generated by said active aptamer. The intramolecular reconfiguration sequence can comprise a Broccoli aptamer. The optically detectable output generated by said active aptamer can be a fluorescence signal. The RNA-target binding sequence can be located in a loop component of a hairpin structure. The RNA-target binding sequence can be a toehold domain. The intramolecular reconfiguration sequence can comprise a tRNA aptamer scaffold comprising an inactive aptamer and a tRNA scaffold, said probe configured such that binding of a RNA target by said RNA-target binding sequence triggers said intramolecular reconfiguration sequence to form a tRNA-stabilized active aptamer such that an optically detectable output is generated by said active aptamer. The intramolecular reconfiguration sequence can comprise two or more tRNA aptamer scaffolds. When activated, the two or more tRNA aptamer scaffolds can generate fluorescence signals of two or more colors. The intramolecular reconfiguration sequence can comprise two tRNA aptamer scaffolds, each of the two tRNA aptamer scaffolds flanking a central toehold domain. The optically detectable output generated by said probe can be an increase in RNA stability or resistance to nuclease degradation, which results in an increase in fluorescence.

In another aspect, provided herein is a molecular fuse imaging probe comprising a single RNA polynucleotide comprising an RNA-target binding sequence and a plurality of aptamers, wherein each aptamer of the plurality comprises a hairpin structure, said probe configured such that binding of a RNA target by said RNA-target binding sequence triggers an intramolecular reconfiguration whereby each aptamer of the plurality is activated and an optically detectable output is generated by said active aptamer. The single RNA polynucleotide can comprise two or more hairpins, where hairpins at the 5' end of the polynucleotide have single-stranded toehold interaction domains at the 5' end of each hairpin, and where hairpins at the 3' end of the polynucleotide have single-stranded toehold interaction domains at the 3' end of each hairpin, said probe configured such that binding of an RNA target by said RNA-target binding sequence triggers an intramolecular reconfiguration and yields a long partially double-stranded RNA (dsRNA) product. The single RNA polynucleotide comprises two or more hairpins, wherein hairpins at the 5' end of the polynucleotide have single-stranded toehold interaction domains at the 3' end of each hairpin, and wherein hairpins at the 3' end of the polynucleotide have single-stranded toehold interaction domains at the 5' end of each hairpin, said probe configured such that binding of an RNA target by said RNA-target binding sequence triggers an intramolecular reconfiguration and yields a long partially double-stranded RNA (dsRNA) product. The single RNA polynucleotide can comprise two or more hairpins comprising single-stranded toehold interaction domains at the 5' end of each hairpin, said probe configured such that binding of a RNA target by said RNA-target binding sequence triggers an intramolecular reconfiguration and yields a multi-armed RNA junction product. The single RNA polynucleotide can comprise two or more hairpins comprising single-stranded toehold interaction domains at the 3' end of each hairpin, said probe configured such that binding of an RNA target by said RNA-target binding sequence triggers an intramolecular reconfiguration and yields a multi-armed RNA junction product. The single RNA polynucleotide can comprise two or more hairpin-like structures comprising inactive aptamers, said probe configured such that binding of an RNA target by said RNA-target binding sequence triggers an intramolecular reconfiguration that causes the stem domain of each hairpin to hybridize with the stem domain in an adjacent hairpin-like structure to form two or more active aptamers.

In another aspect, provided herein is a method for imaging RNA in a live cell, the method comprising introducing into said live cell a RNA polynucleotide comprising an RNA-target binding sequence and an intramolecular reconfiguration sequence, said probe configured such that binding of a RNA target by said RNA-target binding sequence triggers said intramolecular reconfiguration sequence to reconfigure to form an active aptamer such that an optically detectable output is generated by said active aptamer; and detecting said output if said RNA target is present in said live cell. The RNA target can comprise a single RNA molecule within a single live cell.

BRIEF DESCRIPTION OF THE DRAWINGS

FIG. 6 illustrates embodiments of molecular fuses based on domain-flipping cascades. Domain-flipping cascades make use of an engineered RNA than can exist in bright and dark near-equilibrium states. The dark state consists of a series of misfolded reporter aptamer domains, while the bright state consists of the reporter aptamers in their properly folded configurations. A 5' hairpin in the molecular fuse is used to lock the domain-flipping region into its dark state in the absence of the target RNA. Once the target RNA for imaging binds through a loop-mediated interaction, the hairpin repression is relieved and the domain-flipping region is able to adopt the thermodynamically preferred bright configuration and turn the fuse on.

DETAILED DESCRIPTION

Figure 1:
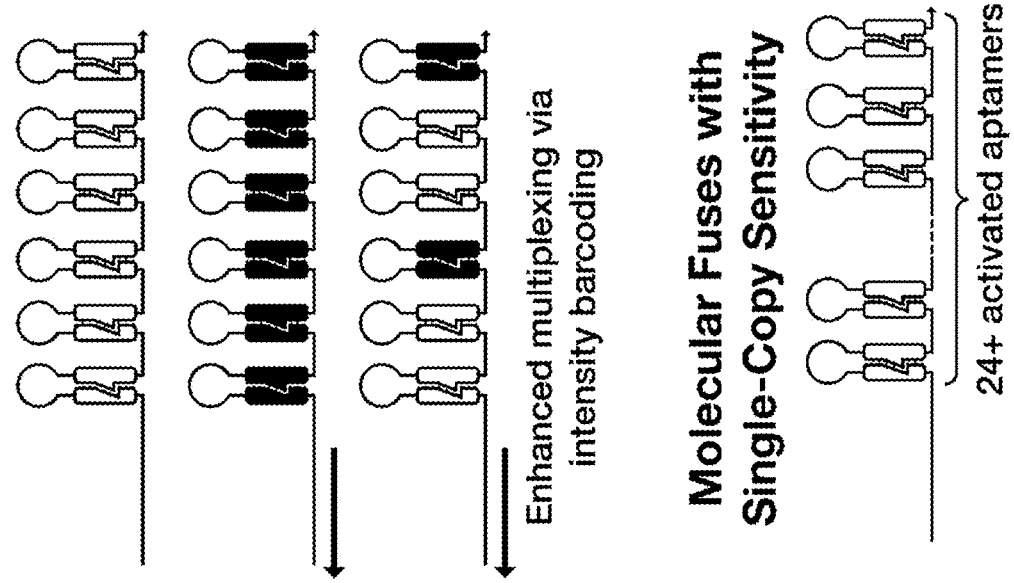
FIG. 1 is a schematic depicting genetically encoded RNA imaging probes that employ intramolecular chain reactions to provide multiplexed RNA imaging down to the single-copy level.
Figure 1:
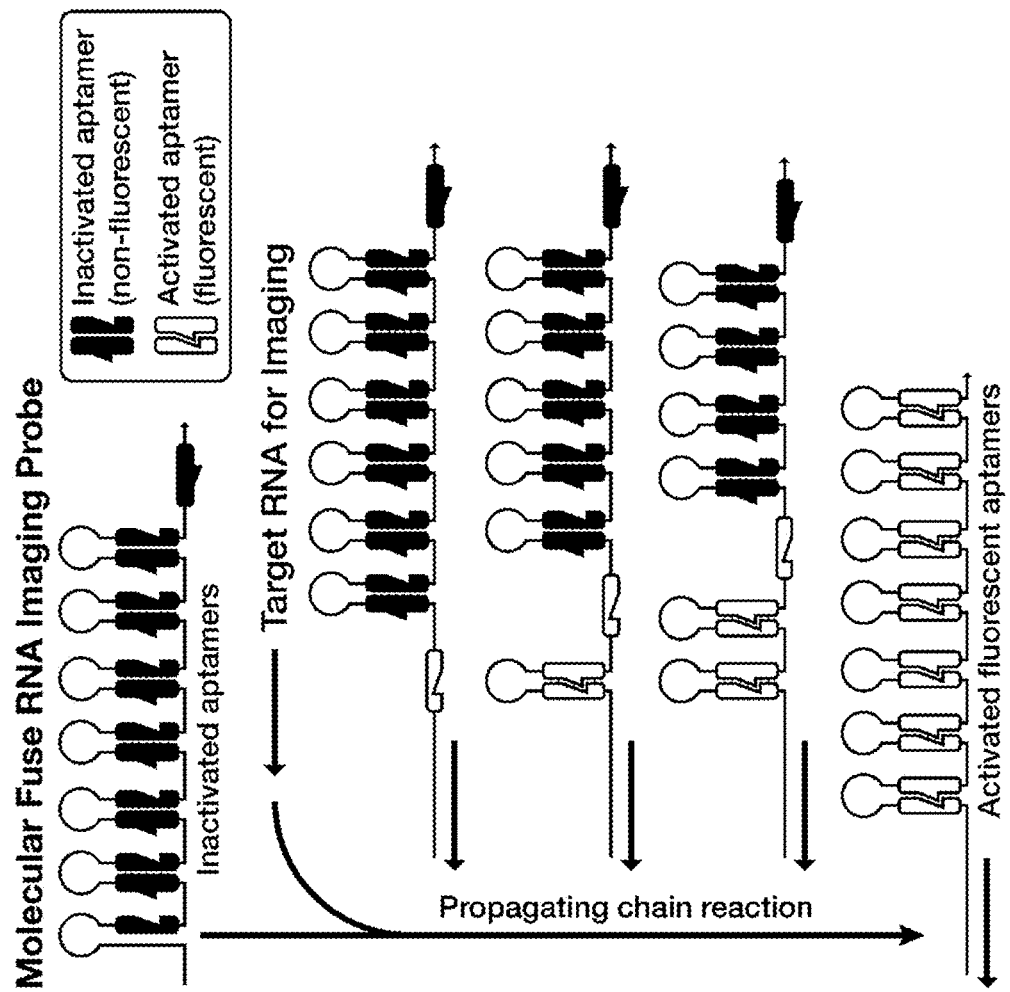

All publications, including but not limited to patents and patent applications, cited in this specification are herein incorporated by reference as though set forth in their entirety in the present application.

Existing live-cell RNA imaging techniques have thus far failed to provide an optimal combination of genetic encoding and strong multiplexing capabilities. Moreover, genetically encoded probes have strikingly failed to take advantage of arguably the most powerful property of RNA as a biomaterial—its ability to predictably base pair via Watson-Crick interactions.

The RNA-based imaging probes, systems, and methods provided herein are based at least in part on the inventors' development of two new paradigms for nucleic acid self-assembly and new capabilities for RNA imaging and detection. The systems and methods provided herein are effective aptamer-based systems for label-free, highly multiplexed, real-time nucleic acid imaging in live cells. These systems generally make use of aptamers that either bind to conditionally fluorescent dye molecules (e.g., Broccoli/DFHBI-1T) or can be used to bind to domains fused to fluorescent proteins (e.g., MS2 aptamer/MS2 protein-GFP fusions). As described herein, these systems employ aptamer-based sensor designs that trigger the formation of functional aptamers in response to the binding of target nucleic acids. As used herein, the terms "aptamer-based sensors" and "aptasensor" refer to molecular sensors that bind to a target analyte (e.g. an endogenous RNA) and refold into an active ("ON") state aptamer structure. Molecular fuses in turn consist of arrays of aptasensors that undergo intramolecular reactions that cause them to switch from an inactive OFF state to an active ON state.

As used herein, the term "aptamer" refers to nucleic acids or peptide molecules that are capable to bind a specific target. In particular, aptamers can comprise single-stranded (ss) oligonucleotides and peptides, including chemically synthesized peptides. Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc.

RNA is the ideal biomaterial to image RNA inside the cell. Our molecular fuse probes capitalize on all the properties below to enable real-time, label-free, multiplexed RNA imaging in live cells. For instance, RNA-RNA interactions are specific and fast. The predictability of Watson-Crick base-pairing interactions ensures that RNAs can interact specifically with target RNAs. It further ensures that these interactions occur rapidly over sub-millisecond time scales facilitating intramolecular cascades. In addition, RNA binds multiple ligands. There is a diverse library of RNAs known to bind to small-molecule ligands and proteins via aptamers. These RNA modules can serve as labels for live-cell imaging. Since RNA is a transient information carrier, RNA-based probes are much more likely to faithfully capture dynamics of RNA expression and degradation than protein- and DNA-based imaging probes. Moreover, single-stranded RNA is routinely expressed inside the cell. Single-stranded DNA expression, on the other hand, requires more exotic approaches. Sophisticated software packages have already been developed for generating RNA sequences that adopt a desired secondary structure and vice versa. The in silico design and analysis capabilities for RNA as described herein are much more advanced than equivalent tools for proteins. Finally, long single-stranded RNA is readily synthesized. Self-assembly approaches developed in DNA nanotechnology have for the most part focused on using short (<100-nt) synthetic DNA strands. It is simply challenging to produce long, non-repeating single-stranded DNA. Long single-stranded RNA is routinely made from double-stranded DNA templates in vitro and in vivo. Synthetic DNA templates can be integrated into the genome to express long RNAs within the cell, avoiding the challenges of nucleic acid delivery.

In view of the above, the imaging probes disclosed herein include an intramolecular reconfiguration sequence, which in an embodiment, comprises a tRNA scaffold. As used herein, the term "intramolecular reconfiguration sequence" refers to intramolecular domains designed to reconfigure themselves into one or more active output aptamers upon binding on the target RNA to the probe. The optically detectable output generated by such probes is due to formation of an active aptamer fold, which triggers fluorescence; and/or an increase in RNA stability, or in resistance to nuclease degradation, which results in an increase in fluorescence.

Aptasensor Imaging Probes and Systems

Accordingly, in a first aspect, provided herein are aptamer-based sensors ("aptasensors") and aptasensor systems comprising triggerable RNA molecules engineered to form active (functional) aptamers in response to target RNA binding. Aptasensors provided herein are capable of binding directly to native RNAs in a live cell and emitting fluorescence for imaging RNA at its subcellular location. The aptasensors provided herein, therefore, are improved over existing aptasensors. Previous aptasensors have been unable to operate effectively in live cells since they required modified bases that could not be synthesized by the cell and thus required transfection, were unable to recognize diverse RNA sequences, were unstable in the intracellular environment, or were unable to provide sufficiently bright fluorescence for imaging. A subclass of aptasensors that modulate their intracellular stability (see full description below) are used to respond to the challenge of generating long-lived, stable imaging probes and molecular fuses are used to resolve the challenge of generating bright imaging probes for RNA visualization in live cells.

Figures 2A, 2B, 2C, 2D, 2E:
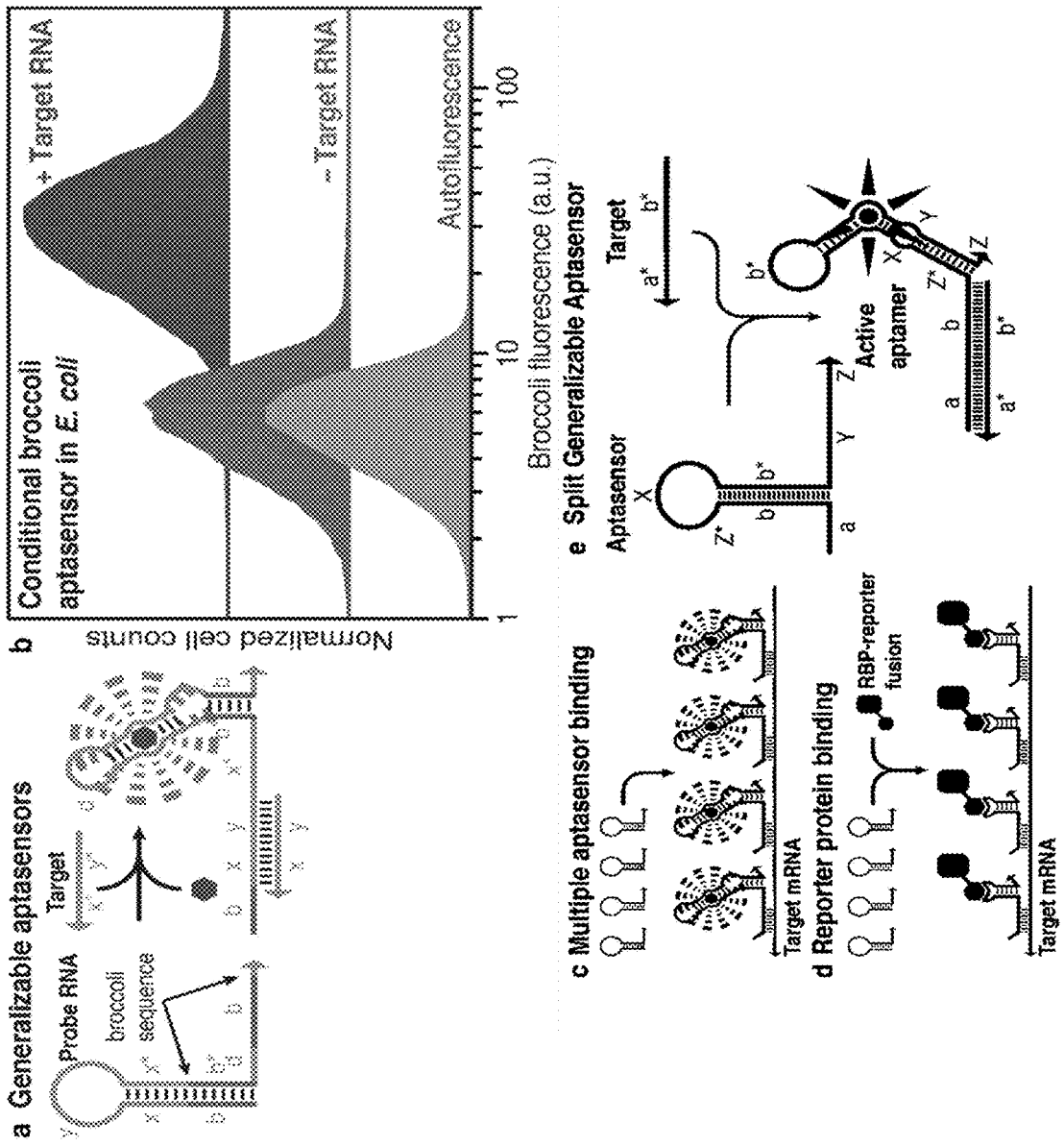
FIG. 2A illustrates a generalizable aptasensor mechanism implemented with a Broccoli aptamer.
FIG. 2B demonstrates in vivo characterization of a functional Broccoli aptasensor in *E. coli*, using aptasensor RNA sequences SEQ ID NOs:1, 3, 5, and 7 relating to target RNA sequences SEQ ID Nos:2, 4, 6, and 8, respectively.
FIG. 2C demonstrates multi-probe approaches for imaging single-copy RNAs in vivo using fluorescent aptasensors.
FIG. 2D demonstrates multi-probe approaches for imaging single-copy RNAs in vivo using protein-binding aptasensors.
FIG. 2E illustrates design of a split generalizable aptasensor where the aptamer is cut in two separated domains.

To facilitate integration with molecular fuses, aptasensors are ideally capable of detecting RNAs with arbitrary sequences. In certain embodiments, therefore, the aptasensors are generalizable, meaning that, in principle, the aptasensor will be compatible with any output aptamer while enabling detection of arbitrary nucleic acid sequences. More particularly, generalizable aptasensor systems can be studied in cultured cells using a fluorescent aptamer such as Broccoli as the output aptamer. The Broccoli/DFHBI-1T system is ideal for aptasensor studies since triggered formation of the aptamer results in detectable fluorescence from cells (FIG. 2A). In the untriggered state, the aptasensor contains a hairpin with an extended loop domain that serves as an initial hybridization region for binding to the target RNA. This hairpin is fused to the conserved sequence of the inactivated aptamer. Importantly, the output domain b* in the hairpin has no sequence overlap with the cognate target RNA, enabling b* to take on the sequence of the output aptamer. Upon target binding, the loop-mediated target-aptasensor interaction functions as a molecular crowbar that breaks apart bases lower in the stem. The newly exposed b* domain in turn enables the aptamer to refold into its active configuration by binding to the free b domain at the 3' end of the aptasensor. This molecular design enables the aptasensor to regulate any aptamer of interest and respond to any target RNA sequence.

The generalizable aptasensor designs provided herein are useful in both in vitro and in vivo contexts. As shown in FIG. 2B, flow cytometry was performed to detect fluorescence from E. coli comprising an aptasensor comprising the Broccoli aptamer with its tRNA scaffold for increased RNA stability (see full description below of structure-switching aptasensors). Substantial increases in Broccoli/DFHBI-1T fluorescence were detected when the aptasensor probe was expressed with its cognate target RNA trigger, while fluorescence was near background levels in the absence of the cognate RNA trigger.

In some cases, the lengths of domains a, b, and c are varied to increase the probe's signal-to-noise ratio. In some cases, other aptamers are used including, without limitation, MS2, PP7, and lambdaN RNA domains routinely used for RNA binding protein attachment. In other cases, additional aptamer/dye and aptamer/quencher systems for new output fluorescence signals can be used. To lower the detection limit of the aptasensors, it can be advantageous to use multiple aptasensors that bind along different portions of a target RNA (see FIGS. 2C, 2D).

Alternative generalizable aptasensor designs can be used. For example, as shown in FIG. 2E, the output aptamer can be divided in two and half the aptamer is sequestered in a loop domain. In this configuration, binding of the target RNA binds to the aptasensor frees loop domains X and Z', which are then available to refold into the ON state aptamer. This design provides easier integration into some molecular fuse designs described below and enables improved specificity.

The generalizable aptasensor design described herein deploys loop-mediated interactions to begin the aptasensor-trigger interaction. Such interactions are advantageous in terms of specificity and design modularity, suggesting this new paradigm will be broadly useful in self-assembled nucleic acid systems.

Figure 2F:
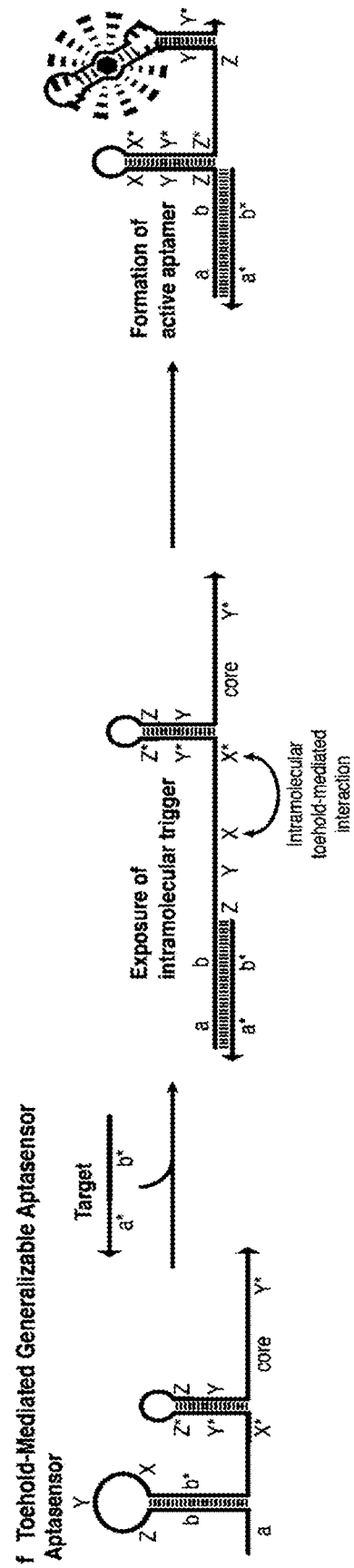
FIG. 2F illustrates design of toehold-mediated aptasensor that employs intramolecular trigger domains X, Y, and Z to cause formation of an active aptamer while preserving substantial sequence flexibility.

Another generalizable design is illustrated in FIG. 2F. This design, called a toehold-mediated generalizable aptasensor design, combines features of the designs shown in FIG. 2A and FIG. 2E. When configured according to the toehold-mediated generalizable design, a hairpin comprising a 5' toehold domain serves as a recognition site for the target RNA. Upon binding of the aptasensor and target RNA, the loop domains X, Y, and Z are freed upon stem unwinding. The X, Y, and Z sequence in turn serves as an intramolecular trigger to unwind a downstream hairpin that was preventing formation of the aptamer. The mechanism of this aptasensor employs toehold-mediated strand displacement reactions, which are well-characterized and very kinetically favorable. Furthermore, since the X domain in the loop is not sequence constrained, it can take a sequence that encodes conserved bases in the aptamer. Overall, the design in FIG. 2F is useful for detecting arbitrary nucleic acid sequences, does not modify the aptamer sequence, and employs rapid toehold-mediated reactions, which are three very desirable properties for an RNA sensor in the cell.

In certain embodiments, aptasensors of this disclosure comprise aptamers that bind a dye molecule to induce fluorescence. In other cases, the aptasensors comprise aptamers that bind a protein reporter to label the target RNA. When the aptamers bind to the dye molecule or protein reporter, the aptasensor labels the target RNA for imaging.

In some cases, the aptasensors are genetically encoded, meaning that the imaging probes are produced within the cell, thus lowering their cost and removing the requirement for delivery from outside of the cell. These features are key advantages over molecular beacons and smart flares.

In certain embodiments, the aptasensors provided herein comprise fluorescent aptamers. Any appropriate fluorescent aptamer can be used for aptamer-based sensors ("aptasensors") described herein. For example, the fluorescent RNA aptamer can be Broccoli. As used herein, the term "Broccoli" or "Broccoli aptamer" refers to a 49-nt fluorescent RNA aptamer-fluorophore complex (see Filonov et al., *J. Am. Chem. Soc.* 2014, 136(46):16299-16308) that confers fluorescence to a target analyte (e.g., target RNA) of interest via activation of the bound fluorophore DFHBI or a DFHBI-derived fluorophore such as (Z)-4-(3,5-difluoro-4-hydroxybenzylidene)-2-methyl-1-(2,2,2-trifluoroethyl)-1H-imidazol-5(4H)-one) (DFHBI-1T) as described by Song et al., *J. Am. Chem. Soc.* 2014, 136:1198. Other fluorescent RNA aptamers that can be used include, without limitation, Spinach and Spinach2 (Strack et al., *Nature Methods* 2013, 10:1219-1224), Carrot and Radish (Paige et al., *Science* 2011, 333:642-646), RT aptamer (Sato et al., *Angew. Chem. Int. Ed.* 2014, 54:1855-1858), hemin-binding G-quadruplex DNA and RNA aptamers, and malachite green binding aptamer (Babendure et al., *J. Am. Chem. Soc.* 2003). Several new alternatives to the Broccoli aptamer were recently reported by Song et al., *Nature Chemical Biology* 13, 1187 (2017). These aptamers all bind to the molecule 3,5-difluoro-4-hydroxybenzylidene-imidazolinone-2-oxime (DFHO), which resembles the fluorophore of red fluorescent protein (RFP), and thus provide red-shifted fluorescence compared to the green emission from Broccoli when it binds to DFHBI-1T. The new DFHO-binding aptamers are named Corn, Red Broccoli, and Orange Broccoli. As will be understood by practitioners in the art, selection of a fluorescent RNA aptamer-fluorophore complex for use in an aptasensor described herein will depend on fundamental properties of the aptamer such as brightness (or enzymatic output), folding properties, and amenability to sequence modifications.

In other cases, the aptasensors provided herein comprise colorimetric aptamers. In such cases, the presence and location of the target nucleic acid is indicated by a color change. Any appropriate colorimetric aptamer can be used. The term "colorimetric" is defined as an analysis where the reagent or reagents constituting the aptasensors system produce a color change in the presence or absence of an analyte. The degree the color changes in response to the analyte (e.g., target nucleic acid) may be quantified by colorimetric quantification methods known to those of ordinary skill in the art in. In some cases, standards containing known amounts of the selected analyte may be analyzed in addition to the sample to increase the accuracy of the comparison.

Figures 5A, 5B, 5C:
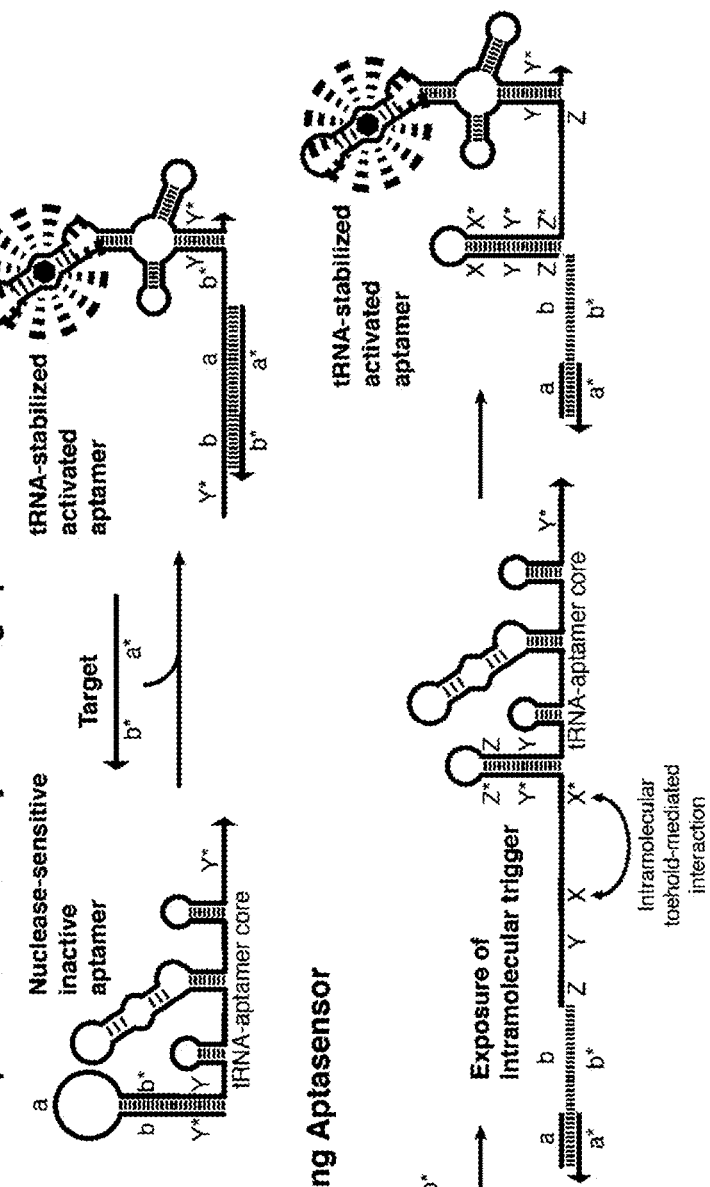
FIG. 5A is schematic illustrating an aptamer/tRNA scaffold fusion. The tRNA scaffold confers enhanced nuclease resistance to an aptamer fused to its upper stem, which thereby increases its intracellular lifetime.
FIG. 5B illustrates design of a loop-mediated stability-switching aptasensor in which the target RNA binds to the loop of the aptasensor to cause formation of the tRNA scaffold.
FIG. 5C illustrates design of a toehold-mediated stability-switching aptasensor in which the target RNAs to the toehold of the aptasensor to initiate intramolecular reactions that lead to formation of the tRNA scaffold.

In certain embodiments, the aptasensors provided herein are stability-switching aptasensors. Application of aptasensors described in previous disclosures for intracellular imaging can thus be challenging if the aptasensors are unable to withstand RNase activity in the cell and rapidly lose their fluorescence. Compared to conventional aptasensors, which can be hampered by instability and rapid degradation by RNases in the cell, stability-switching aptasensors as described herein exploit differences in RNA stability to facilitate live-cell RNA imaging. As shown in FIG. 5A, stability-switching aptasensors make use of tRNA scaffolds that have been widely used to protect cellular RNAs from degradation. The tRNA scaffolds comprise the nucleic acid sequence of cellular tRNAs and thus their tertiary structure can be recognized by the enzymes responsible for tRNA maturation. Importantly, the scaffolds also provide an open stem domain that can be used for fusions to an output aptamer of interest, such as a fluorescent aptamer/dye complex (FIG. 5A). Thus, RNAs with a tRNA scaffold can confer a marked increase in intracellular stability for their aptamer fusions compared to typical RNAs that are subject to much faster degradation pathways.

In some cases, a stability-switching aptasensor is configured to adopt a correctly folded tRNA scaffold structure in its activated ("ON") state (i.e., upon binding to the target RNA) and a misfolded tRNA scaffold structure in its unactivated ("OFF") state. When such an aptasensor is expressed in the absence of its cognate target RNAs, the misfolded tRNA scaffold leaves the aptasensor vulnerable to degradation by intracellular RNases and, thus, no fluorescent or other detectable signal is emitted. Upon binding of a stability-switching aptasensor to its target RNA, the correctly folded tRNA scaffold is processed as a cellular tRNA, which prolongs its retention in the cell. In this manner, the stability-switching aptasensor is useful for marking the presence and subcellular location of a target RNA in a cell via emission of a reporter signal by a fluorescent aptamer/dye complex or other detectable means.

Referring now to the various stability-switching designs illustrated in FIGS. 5B-5E, stability-switching aptamers can employ different target-aptasensor interactions and different numbers of output aptamers. In the loop-mediated stability-switching aptasensor design shown in FIG. 5B, proper folding of the tRNA scaffold is prevented by sequestering the bottom stem domain Y of the scaffold within a very stable stem-loop structure. This stem-loop features an extended loop domain of approximately 15 to 24 nts that is available for binding to a cognate target RNA with the complementary sequence. When the target RNA is present, its a* domain initially hybridizes with the a domain of the loop and proceeds to disrupt the duplex region of the stem-loop by binding through its b* domain. Disruption of the stem in turn releases the Y domain of the tRNA scaffold, which then hybridizes to the complementary Y* domain at the 3' end of the aptasensor. After the Y-Y* stem is formed, the tRNA scaffold now exists in its properly folded state and can then be processed as a tRNA to increase its intracellular lifetime substantially. It is important to note that the loop-mediated interaction scheme is essential to enable the aptasensor to detect arbitrary RNA targets since the sequences of the tRNA scaffold and its Y-Y* stem are typically conserved to ensure proper processing. We have confirmed successful RNA detection in living *E. coli* cells using loop-mediated stability-switching aptasensors using flow cytometry and the Broccoli aptamer. Data from these experiments is shown in FIG. 2B, using aptasensor RNA sequences SEQ ID NOs:1, 3, 5, and 7 relating to target RNA sequences SEQ ID Nos:2, 4, 6, and 8, respectively. In the absence of the target RNA, the structure-switching aptasensor provides low fluorescence, while addition of the target RNA shows a roughly five-fold increase in fluorescence.

Although toehold-mediated interactions are highly desirable thermodynamically and kinetically, direct use of such interactions in the stability-switching aptasensors is challenging as a result of sequence constraints imposed by the tRNA scaffold. It is possible, however, to adapt the toehold-mediated generalizable aptasensor design shown in FIG. 2F to generate toehold-mediated stability-switching aptasensors. The design of these toehold-mediated systems relies on two hairpins, located at the 5' end and in the middle of the aptasensor, to enable triggered formation of the stabilizing tRNA structure (FIG. 5C). The 5' hairpin has a 5' toehold domain and is used for detecting the complementary target RNA. The middle hairpin also has a 5' toehold and sequesters the Y domain of the tRNA scaffold, which prevents proper folding of the tRNA sequence remaining downstream. When the target RNA is present, it initially binds to the 5' hairpin and unwinds its stem. This interaction in turn frees a loop domain whose sequence is completely independent from that of the target RNA. This released loop sequence then serves as an intramolecular trigger that binds through a second toehold-mediated interaction to unwind the hairpin in the middle of the aptasensor. Disruption of the middle hairpin releases the Y domain, which finally allows the full tRNA scaffold to assemble and stabilizes the reporter aptamer.

It is worth noting that the loop-mediated and toehold-mediated stability-switching aptasensors can be designed such that the intramolecular reactions run from the 3' to 5' direction rather than the 5' to 3' direction depicted in FIGS. 5B-5C. Such 3' to 5' systems would essentially reverse the order of the domains depicted in FIGS. 5B-5C with some changes to this prescription owing to the sequence constraints of the tRNA scaffold.

Figures 5D, 5E:
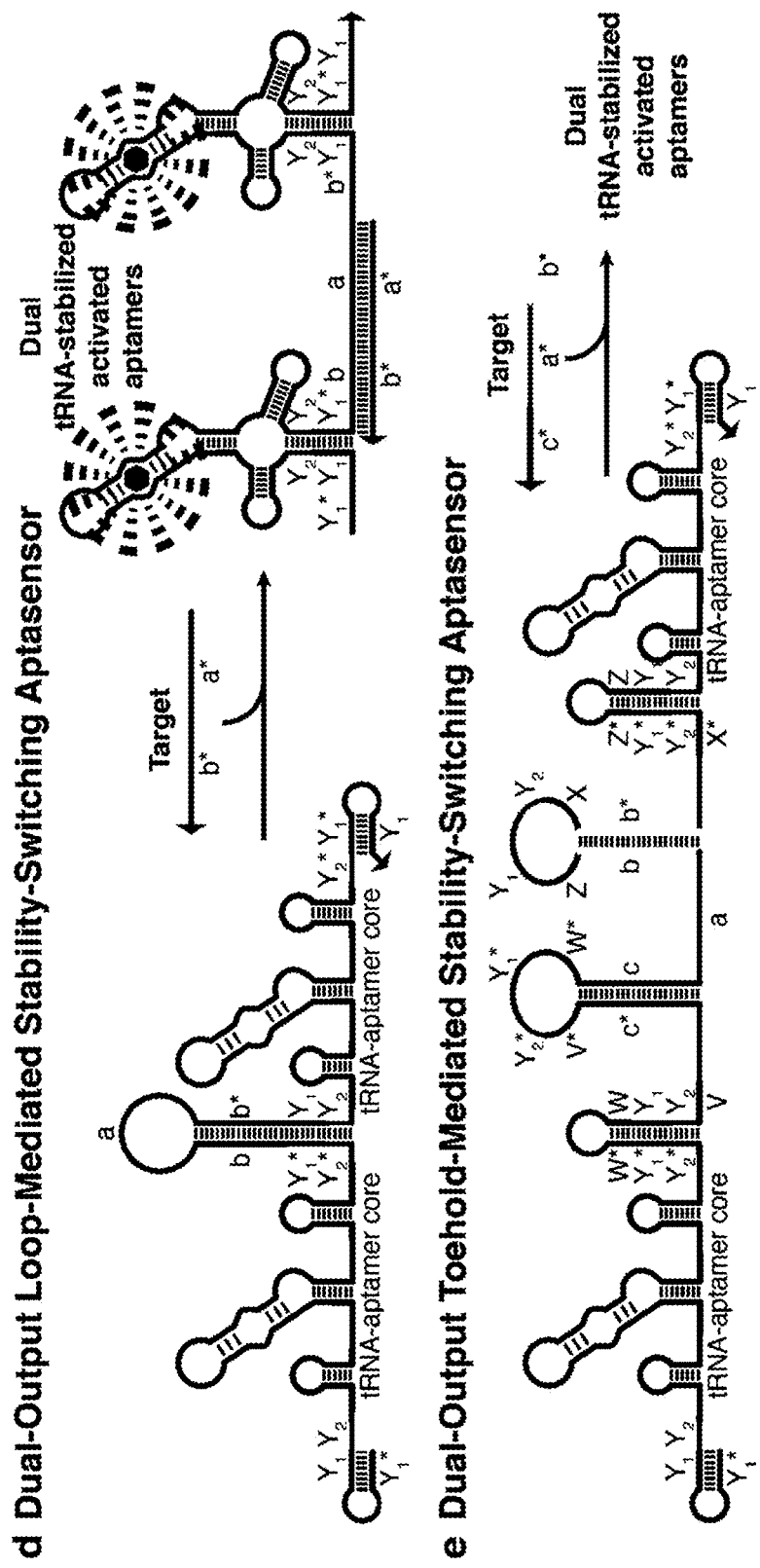
FIG. 5D illustrates design of a dual-output loop-mediated stability-switching aptasensor that forms two tRNA-stabilized aptamers following binding of a single target RNA.
FIG. 5E illustrates design of a dual-output toehold-mediated stability-switching aptasensor.

The reversibility of the two aptasensor designs also enables us to generate systems in which the binding of a single target RNA activates two output aptamer modules. An example of such a system is shown in FIG. 5D, where the loop-mediated stability-switching aptasensor is used to activate a pair of aptamer/tRNA scaffold fusions. The dual-output aptasensor contains a central stem-loop engineered to bind to a complementary target RNA. Target binding disrupts the stem-loop and releases two pairs triggering domains. Domains $Y_1^*$ and $Y_2^*$ are released to bind to complementary $Y_1$ and $Y_2$ domains near the 5' end of the aptasensor in a toehold-mediated intramolecular interaction. Similarly, domains $Y_1$ and $Y_2$ are released to bind to $Y_1^*$ and $Y_2^*$ domains near the 3' end in a second toehold-mediated intramolecular interaction. Binding of these intramolecular triggers enables formation of the complete tRNA scaffold and, in turn, stabilizes the two output aptamers. The 5' and 3' ends of the aptasensor employ short $Y_1$-$Y_1^*$ stem-loop domains to discourage direct binding of the $Y_1/Y_2$ and $Y_1^*/Y_2^*$ in the absence of the target RNA, which otherwise could lead to non-specific aptasensor activation. The dual-output aptasensor can also be implemented using a toehold-mediated mechanism by fusing a 3' to 5' and a 5' to 3' aptasensor via a central toehold domain as illustrated in FIG. 5E.

In some cases, a stability-switching aptasensor comprises one or more other RNA motifs including, without limitation, a hairpin, G quadruplex, and 5'-OH terminus caused by ribozyme cleavage.

Molecular Fuse Imaging Probes and Systems

In another aspect, provided herein are molecular fuses. As used herein, the "molecular fuse" refers to a single triggerable RNA molecule comprising multiple aptasensors that form multiple, potentially dozens, of functional aptamers through intramolecular chain reactions when triggered by binding to a single target RNA. Advantageously, molecular fuses offer a solution to the problem of low fluorescence output from an aptamer once it is activated. As illustrated in FIG. 1, upon binding to a single target RNA, the molecular fuse undergoes a domino-like intramolecular chain reaction that causes each of the fuse's constituent aptamers to refold into its active ON state, capable of capturing a ligand and emitting fluorescence. The intramolecular chain reaction within each fuse propagates rapidly along the RNA probe in a series of Watson-Crick base pairing interactions. These interactions are akin to the propagation of a flame along a macroscopic fuse. Without being bound to any particular theory or mode of action, the intramolecular chain reaction amplifies the molecular fuse's fluorescence output, thereby lowering the detection limit of RNA imaging probes and nucleic acid sensors in general. By incorporating different combinations of fluorescent centers, highly multiplexed imaging capability can be obtained. The long reconfigurable RNAs described herein can undergo intramolecular chain reactions. In this manner, a single RNA molecule can encode amplification, catalysis, high reaction kinetics, and programmability—features not achievable using conventional self-assembly approaches.

In some cases, the molecule fuse imaging probe comprises a single RNA polynucleotide comprising an RNA-target binding sequence and a plurality of aptamers, where each aptamer of the plurality comprises a hairpin structure, said probe configured such that binding of a RNA target by said RNA-target binding sequence triggers an intramolecular reconfiguration whereby each aptamer of the plurality is activated and an optically detectable output is generated by said active aptamer.

In some cases, the molecular fuses are genetically encoded, meaning that the imaging probes are produced within the cell, thus lowering their cost and removing the requirement for delivery from outside of the cell. These features are key advantages over molecular beacons and smart flares. Unlike existing genetically encoded RNA imaging probes, which enable imaging of at most three RNAs at the same time, highly multiplexed RNA imaging probes based on molecular fuses that have the potential to image dozens of RNAs in a cell at the same time. The multiplexed molecular fuses will activate prescribed combinations of aptamers having different fluorescent ligands using intensity-based barcoding.

Figure 3A:
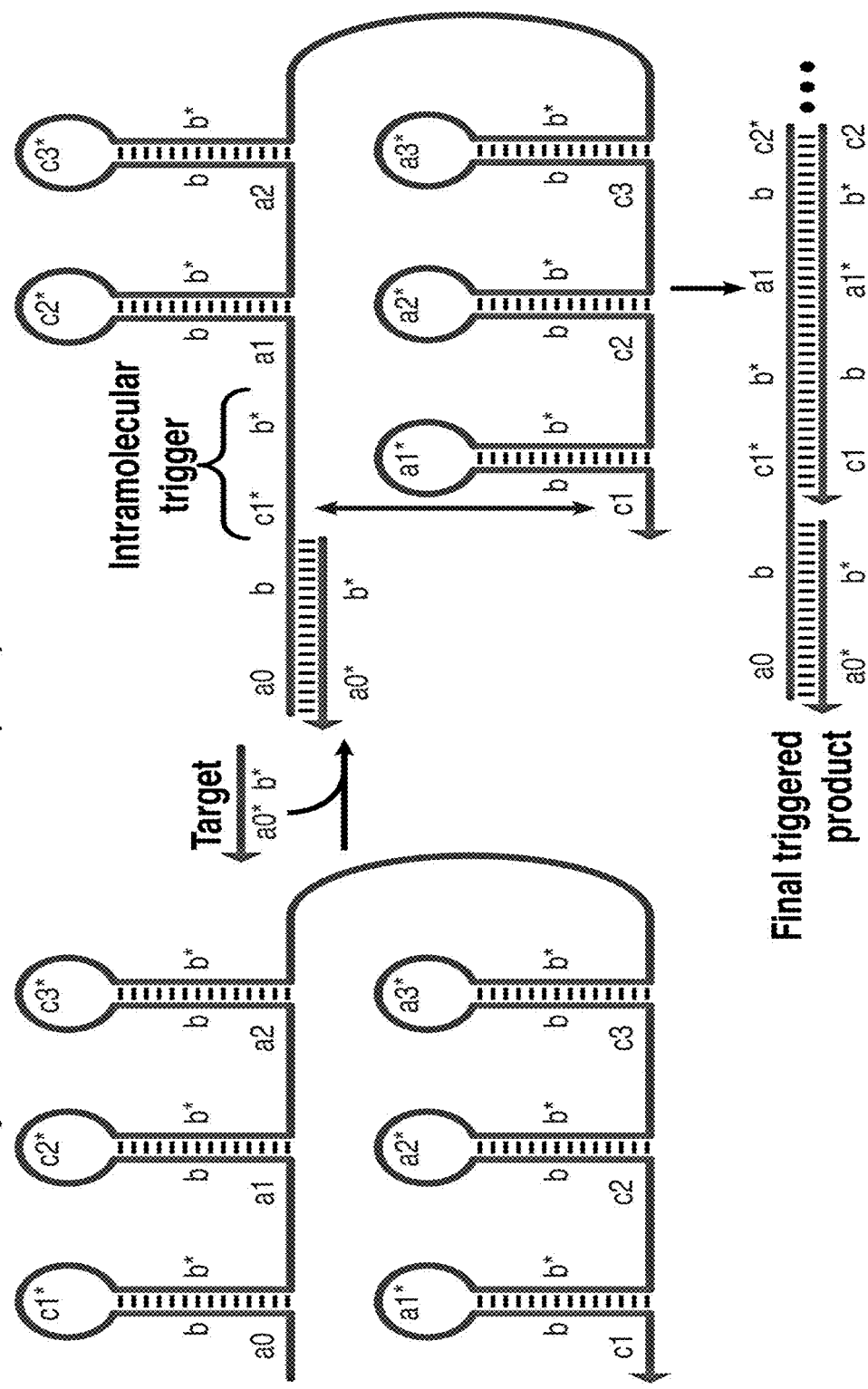
FIGS. 3A-3B illustrate molecular fuse reaction schematics. Dark arrows mark intramolecular interactions. (A) An IHCR system where the final product remains tethered to the target. (B) An ISDC system in which the target RNA can be used repeatedly as a catalyst.
Figure 4:
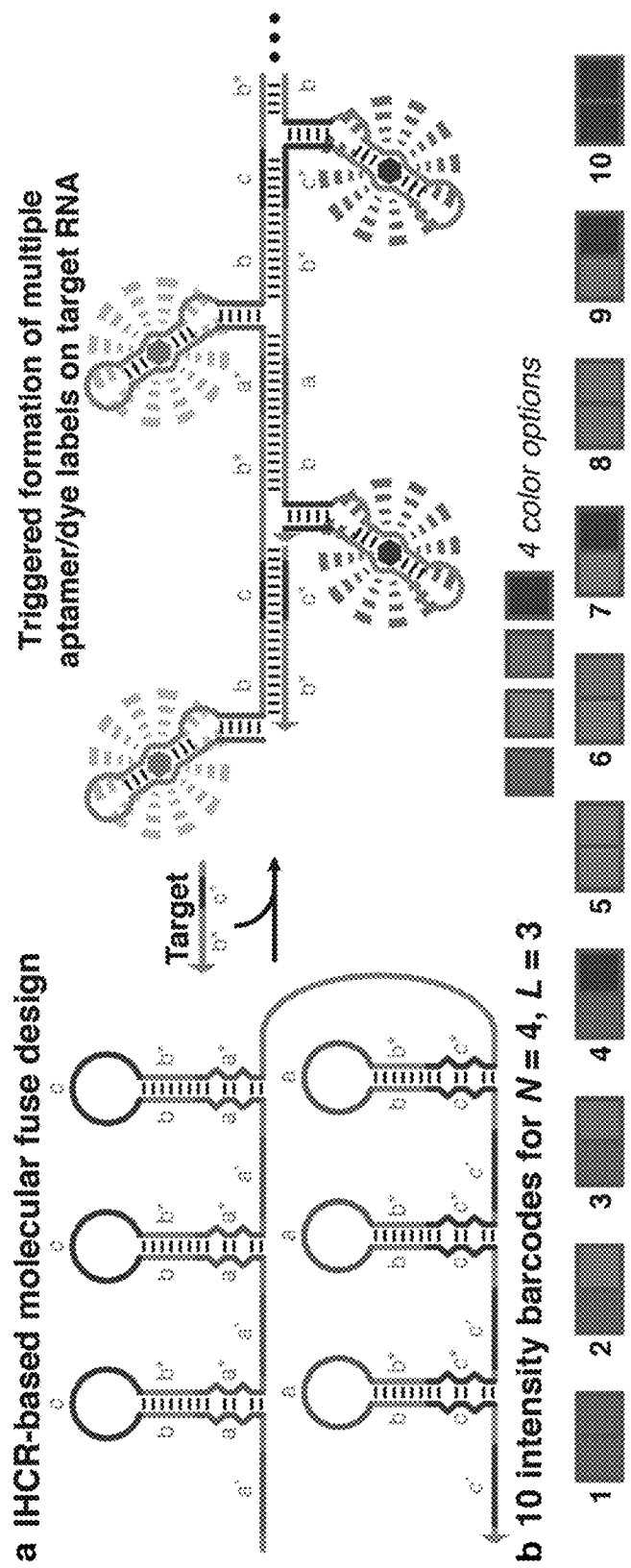
FIGS. 4A-4B illustrate embodiments of IHCR-based molecular fuses having multiplexed intensity barcodes. (A) Schematic of an IHCR system with multiple output aptamers upon triggering. Clamping domains are not shown. (B) Set of 10 resolvable barcodes for N=4 fluorophores and L=3 intensity states. For intensity barcodes, the ordering of the fluorophores does not matter since there is no spatial fluorophore encoding.

In some embodiments, molecular fuses of this disclosure are configured as an intramolecular hybridization chain reaction (IHCR). As shown in FIG. 3A, the IHCR scheme exploits intramolecular interactions at opposite ends of a molecular fuse comprising an array of 2N hairpins, where N is an integer. The first N hairpins have a single-stranded toehold interaction domain at their 5' ends while the last Nhairpins have toeholds at their 3' ends. In the IHCR scheme, the first hairpin is triggered by binding a target RNA through a toehold-mediated branch migration process. The newly exposed hairpin loop and stem domain are then available to undergo an interaction with the downstream 2N hairpin. With each subsequent strand displacement reaction, hairpins closer and closer to one another in the molecular fuse interact and finally form a long double-stranded RNA (dsRNA) product. Loop-mediated interaction mechanisms are also possible with IHCR, as depicted in FIG. 4A.

For IHCR molecular fuses, the single RNA polynucleotide can comprise two or more hairpins, where hairpins at the 5' end of the polynucleotide have single-stranded toehold interaction domains at the 5' end of each hairpin, and wherein hairpins at the 3' end of the polynucleotide have single-stranded toehold interaction domains at the 3' end of each hairpin, said probe configured such that binding of an RNA target by said RNA-target binding sequence triggers an intramolecular reconfiguration and yields a long partially double-stranded RNA (dsRNA) product.

In some cases, the order of intramolecular reactions in an IHCR system is configured such that the reactions proceed from the middle of the probe outwards. In this manner, one may avoid the problem of RNA twisting as the chain reaction proceeds from the outside to the middle of the molecular fuse. In such cases, the single RNA polynucleotide comprises two or more hairpins, wherein hairpins at the 5' end of the polynucleotide have single-stranded toehold interaction domains at the 3' end of each hairpin, and wherein hairpins at the 3' end of the polynucleotide have single-stranded toehold interaction domains at the 5' end of each hairpin, said probe configured such that binding of an RNA target by said RNA-target binding sequence triggers an intramolecular reconfiguration and yields a long partially double-stranded RNA (dsRNA) product.

Figure 3B:
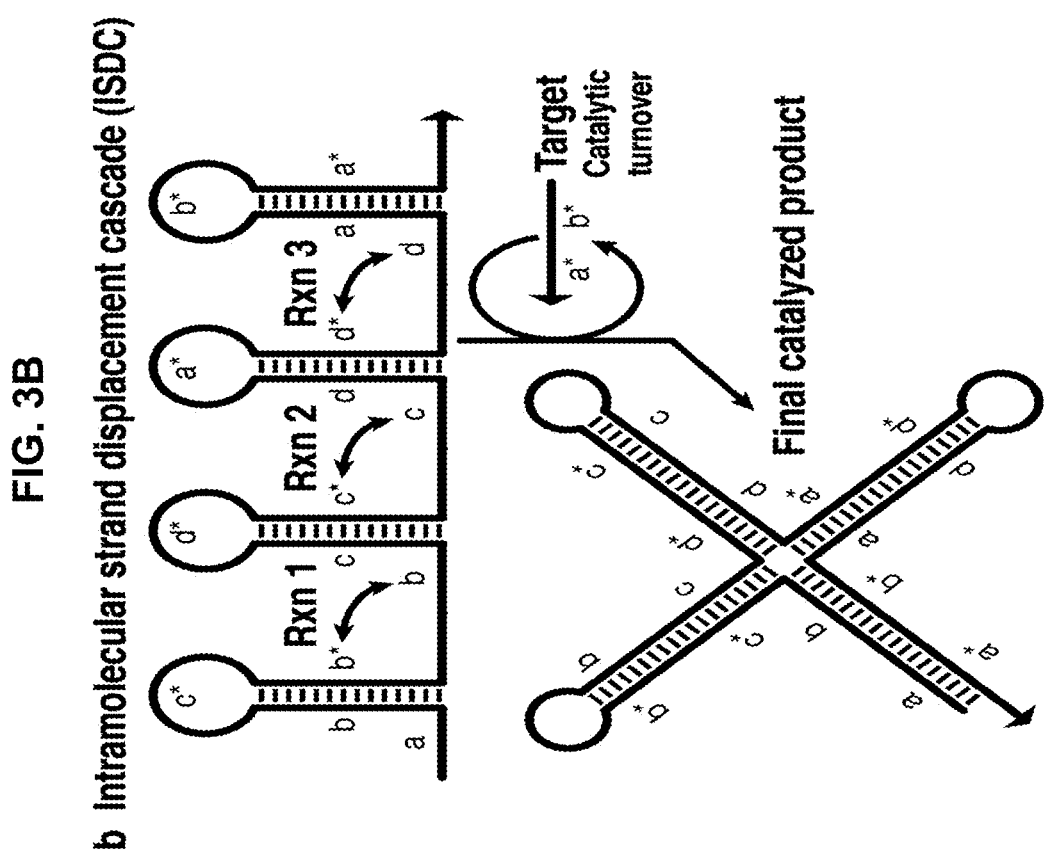

In other embodiments, molecular fuses of this disclosure are configured as an intramolecular strand displacement cascade (ISDC). As illustrated in FIG. 3B, ISDC systems employ interactions between neighboring domains and implement the molecular equivalent of a domino-like chain reaction. Like gate RNAs, ISDC RNAs are composed of an array of hairpins having toehold domains on their 5' ends. When a desired target RNA binds to the first hairpin in the molecular fuse, a downstream interaction domain is exposed and is free to interact with the next hairpin in the RNA. This molecular signaling cascade propagates along the ISDC probe, ultimately forming a multi-armed RNA junction. The cascade can terminate as a self-displacing reaction in which the final RNA structure separates itself from the original target RNA, thereby employing the target RNA as a catalyst that can be reused for multiple reactions without being consumed.

In certain embodiments, the single RNA polynucleotide of a molecular fuse imaging probe comprises two or more hairpins comprising single-stranded toehold interaction domains at the 5' end of each hairpin, said probe configured such that binding of a RNA target by said RNA-target binding sequence triggers an intramolecular reconfiguration and yields a multi-armed RNA junction product.

In other embodiments, the single RNA polynucleotide of a molecular fuse imaging probe comprises two or more hairpins comprising single-stranded toehold interaction domains at the 3' end of each hairpin, said probe configured such that binding of an RNA target by said RNA-target binding sequence triggers an intramolecular reconfiguration and yields a multi-armed RNA junction product.

The designs shown in FIG. 3B have multiple repeating domains that could cause the target RNA to bind at the incorrect location or cause intramolecular refolding to take place in an unintended order. To avoid these effects, non-repeating domains can be used in the molecular fuses to ensure the intended reaction pathway is followed. For certain domains associated with aptamers, it will not be possible to modify sequences; however, neighboring domains can be used to constrain the pathways.

Figure 6:
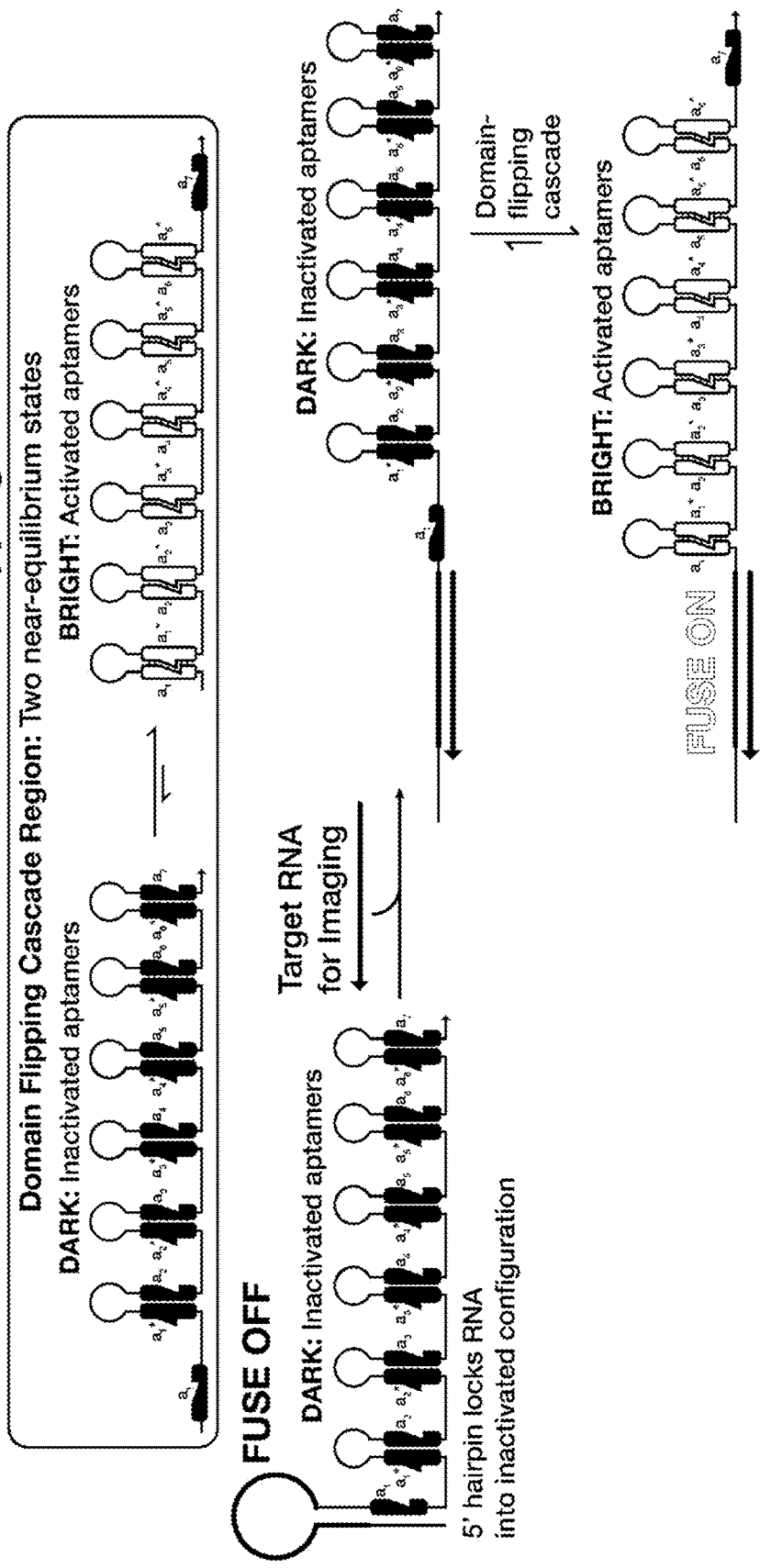

In certain embodiments, the molecular fuse system is configured as a domain-flipping cascade (DFC). As illustrated in FIG. 6, molecular fuses that feature domain-flipping cascades comprise engineered domain-flipping RNA regions that can adopt a bright or a dark near-equilibrium state (see FIG. 6, inset box). The dark inactivated state consists of multiple reporter aptamer domains that are hybridized to one another in misfolded configurations with $a_1'$-$a_2$, $a_2'$-$a_3$, $a_3'$-$a_4$, etc., domain binding. The bright activated state adopts a completely flipped set of configurations with $a_1$-$a_1'$, $a_2$-$a_2'$, $a_3$-$a_3'$, etc., domain binding. In these cognate binding configurations, the reporter aptamer adopts its properly folded state and can be used to bind a dye molecule to emit fluorescence or bind to a fluorescent reporter protein. Through careful design of the $a_1$, $a_1'$, $a_2$, $a_2'$, etc., domains, it is possible engineer the RNA such that the bright configuration is thermodynamically preferred over the dark configuration. This can be done by designing the $a_1$-$a_1'$ interaction such that it has one or two extra base pairs than the $a_1'$-$a_2$ interaction, and by further applying this procedure to the rest of the paired domains in the cascade.

Once the domain-flipping region has been designed computationally, it can be fused with a stem-loop region designed to detect the target RNA for imaging (FIG. 6). This stem-loop region features a long loop domain to efficiently initiate the target-molecular fuse interaction through a loop-mediated mechanism. The stem-loop region also has a long stem domain that contains the $a_1$ domain from the domain-flipping region. By incorporating the $a_1$ domain into a very thermodynamically stable stem, we lock the domain-flipping region into the dark configuration and ensure that the molecular fuse remains in its OFF state. The 5' stem can also be extended to include additional bases from the domain-flipping region to increase the thermodynamic favorability of the OFF state. Once the molecular fuse is able to bind to the target RNA, the loop-mediated interaction causes the stem of the 5' structure to be completely disrupted, relieving the repression of the domain-flipping region. In this intermediate state, the domain-flipping region is now subject to the near equilibrium behavior illustrated in the box in FIG. 6. Consequently, the domain-flipping cascade can propagate through the molecular fuse to flip each of the aptamer domains into their bright configuration, which is more thermodynamically favorable. The net result is the formation of multiple fluorescent sites upon binding to a single target RNA.

In certain embodiments, for molecular fuse imaging probes configured as shown in FIG. 6, the single RNA polynucleotide comprises two or more hairpin-like structures comprising inactive aptamers, said probe configured such that binding of an RNA target by said RNA-target binding sequence triggers an intramolecular reconfiguration that causes the stem domain of each hairpin to hybridize with the stem domain in an adjacent hairpin-like structure to form two or more active aptamers.

The molecular fuses based on domain-flipping cascades can also be configured to activate via toehold mediated interactions. This can be done by fusing the domain-flipping region to a pair of hairpins with 5' toeholds using the general toehold-mediated aptasensor design shown in FIG. 2F. These molecular fuse designs can also be designed in the reverse configuration in which the domain-flipping cascade propagates from 3' to 5' rather than 3' to 5'. Lastly, 5' to 3' and 3' to 5' cascade designs can be integrated into dual output molecular fuses that trigger cascades in both directions using strategies similar to those used for the aptasensors in FIGS. 5B-5E.

Testing of any of the chain-reacting systems described herein (e.g., IHCR, ISDC, and DFC) can be performed by inserting the molecular fuse configuration upstream of existing toehold switches. In this context, the riboregulators serve as sensitive probes of the secondary structure of the upstream RNA. We then measure the output of a GFP reporter protein in *E. coli* in the presence or absence of the target RNA. Systematic studies will determine the optimal domain sizes of the chain-reacting RNA components. We will increase the complexity, and in turn the amplification capabilities, of these systems by adding hairpin modules to the probe RNA. Once optimal design parameters are identified, the intramolecular chain reactions are coupled with the generalizable aptasensors described herein (see FIG. 2A and FIG. 4A).

In some cases, it will be advantageous to first test molecular fuse designs in vitro and then validate measurements in cells (e.g., *E. coli*). Once these initial tests are passed, the most successful fuses are evaluated in vitro (e.g., in mammalian cells via transient transfection) and used to detect synthetic and endogenous cellular RNAs. Different aptasensors can be incorporated into molecular fuse designs to determine variations in probe output as a function of the output aptamer.

In general, molecular fuses are designed and produced by (i) constructing RNA sensors that bind to target RNAs and form output aptamers with different ligands; (ii) developing molecular fuse RNAs that undergo intramolecular chain reactions with RNAs in the cell; (iii) implementing multi-color molecular fuses with combinations of aptamers for multiplexed RNA imaging; and (iv) generating molecular fuses that activate dozens of aptamers for single-molecule RNA imaging.

In view of the above, certain embodiments provided herein are directed to a suite of RNA-based imaging probes that will at last take full advantage of the intrinsic properties of RNA to image this profoundly important biomolecule in a minimally invasive fashion. Furthermore, such embodiments realize the long sought goal to produce genetically encoded systems for imaging multiple RNAs at the same time down to the single-molecule limit.

Molecular fuses address the above problems for conventional self-assembly methods. Each fuse is composed of a single RNA strand that is easy to express and undergoes a series of intramolecular interactions after binding to the targeted endogenous RNA. Encoding RNA interactions within a single molecule ensures that all chain reaction components are co-localized and thus present at high effective concentrations. Furthermore, these high concentrations encourage fast reaction kinetics required for real-time imaging. Lastly, the molecular fuse design enables the encoding of a large amount of information without tradeoffs related to increasing the number of monomers required for self-assembly. More information can be stored in the molecular fuse simply by increasing its length to add more interaction sites to the assembly chain reaction.

For some applications of the embodiments described herein, molecular fuses are genetically encoded imaging probes and are multiplexed for detection of low copy RNAs. Systems of highly multiplexed, genetically encodable live-cell RNA imaging probes offer precisely defined signal gain and can provide multiplexing of 10 to dozens of probes through a novel intensity-based barcoding approach. In certain embodiments, the probes are short enough to make multiplexing and single-copy detection compatible with stable transfection approaches thus avoiding delivery issues.

In other cases, molecular fuses are genetically encoded imaging probes and are useful as unimolecular amplification systems. For example, molecular fuses can be used to develop faster, cheaper, and more sensitive in vitro nucleic acid tests. In certain embodiments, multiple molecule fuses are deployed in one-pot amplification and detection reactions to yield substantial performance gains.

Untriggered molecular fuses adopt a highly metastable structure and could spontaneously refold into the triggered fold without the target. To avoid this issue, molecular fuses can be configured to employ clamping domains to reduce RNA accessibility. In some cases, domains are added to the molecular fuses to modify the energy difference between states. In other cases, molecular fuses are configured to incorporate transcriptional pause sites to encourage folding into the desired secondary structure.

Processing of the molecular fuses through microRNA pathways can be avoided by screening designs for microRNA-associated features. Potential immune responses elicited by dsRNAs can be avoided by intentionally adding bulges into the triggered probe.

Since molecular fuses are encoded within a single RNA expressed from a single promoter, it is quite simple to modify their sequences such that target RNA binding triggers the formation of a prescribed assortment of aptamer labels. Furthermore, once the metastable imaging probe binds to the target RNA there is considerable thermodynamic energy and kinetic programming unleashed in the ensuing intramolecular reconfiguration. As a result, the triggered probe should form output aptamer modules with extremely high yields. These high yields will enable us to assert with high confidence that the target RNA is bound to a precise number of active aptamer species.

We can harness this design feature to produce probes with considerably higher multiplexing capacity than all previous genetically encoded imaging probes. This multiplexing will be enabled through intensity-based barcoding. Based on the current set of fluorescent aptamer/dye systems, it will be possible to construct at least four generalizable aptasensors with four distinguishable fluorescence emission wavelengths (N=4). The intensity of each of these fluorophores in the final triggered probe will then be specified by controlling the numbers of each aptamer formed after the chain reaction. Conservatively, we estimate that we will have three different levels (L=3) of probe fluorescence output intensity (e.g., no fluorescence, half fluorescence, and full fluorescence). This N=4 and L=3 case yields 10 multiplexing channels (FIG. 4B). As the technology increases in sophistication, more aggressive multiplexing with N=4 and L=5 yields 35 distinguishable fluorophores. In some cases, it may be advantageous to employ a CRISPR-Cas9 system to deploy a large number of molecular fuses in the cell at the same time and, thus, avoid the difficulties of stably expressing this combined length of RNA.

To experimentally test these systems, one first conducts in vitro experiments investigating defined combinations of output aptamers and uses a fluorimeter to determine the gradations in brightness produced by each of the aptamers. Once these are measured, increasing numbers of molecular fuses will be expressed using stable cell lines and targeted to mRNAs with known intracellular localization (e.g. SOD2, β-actin, U1). It is important to note that, although the molecular fuses are much longer than many conventional probe systems, such as molecular beacons (~30 nts), they will have lengths ranging from 500 nts up to 3,000 nts, which are commensurate with typical mRNAs. Thus, lentiviruses, which can support payloads of 8 to 10 kb of exogenous DNA, will be able to comfortably integrate eight 1 kb molecular fuses into the genome of HeLa cells. The ultimate length of each molecular fuse will depend on the copy number of the targeted RNA, as more output aptamers will be required to detect lower copy number RNAs.

Existing genetically encoded RNA imaging probes currently require extended RNA labels or tags to enable imaging of single copies of the RNA of interest. These labels in MS2-GFP fusions, for instance, have at least 24 copies of the MS2-binding hairpin and are appended to the 3' end of the RNA of interest. In eukaryotes, where distant enhancer elements influence transcription and zipcode sequences mark mRNA destinations, the addition of these labels can have substantial and unpredictable effects on the behavior of the RNA of interest. To avoid these issues and capture the true behavior of intracellular mRNAs, one can develop molecular fuses that will provide label-free imaging capabilities for target RNAs down to the single-copy level. In some cases, therefore, molecular fuses can be engineered to contain 24 or more output aptamer sites.

In some cases, longer molecular fuses are constructed using gene assembly approaches and tested for function in vitro. For a probe employing Broccoli as output, each copy of the aptamer will contribute approximately 100 nts to the length of the molecular fuse. Consequently, a probe with 24 aptamer copies will yield a molecular fuse of approximately 2.4 kb, which can be integrated comfortably using lentiviruses or using other transfection techniques. In fact, it should be possible to produce even longer molecular fuses with 40+ aptamer sites to increase the sensitivity of the imaging probes beyond MS2-GFP. Since the rate of intramolecular interactions is key to successful use of these extended fuses, we will employ the in vitro tests to measure the rate of probe activation. After in vitro validation, selected molecular fuses can be transiently transfected into cells (e.g., HeLa cells) and targeted to known low-copy mRNAs (e.g., BRCA1).

Given the general capabilities of the proposed molecular fuses, we expect that virtually any target RNA can be imaged using these genetically encoded probes. For example, molecular fuses can be designed to image the dynamics and trafficking of long noncoding RNAs such as Xist, U1, and Malat1 in diploid WI-38 fibroblasts. These three RNAs are known to have different localization patterns, and Xist dynamics will be interesting to study during cell division.

A limitation of the intensity-based barcoding scheme is that it may be challenging to determine the identities of the labeled RNAs in cases where two probes are activated in the same imaging spot. Misidentification can be avoided by implementing algorithms that exclude points with excessive overall imaging label intensity. Alternatively, long reconfigurable probes that undergo triggered assembly can be developed into a geometrically prescribed imaging barcode. The extra degrees of freedom provided by geometric encoding will avoid the bulk of these co-localization events and exponentially increase the number of unique genetically encoded barcodes.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of" when used in the claims, shall have its ordinary meaning as used in the field of patent law.

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

The present invention has been described in terms of one or more preferred embodiments, and it should be appreciated that many equivalents, alternatives, variations, and modifications, aside from those expressly stated, are possible and within the scope of the invention.

We claim:

1. An aptasensor imaging probe comprising:
a ribonucleic acid (RNA) polynucleotide comprising an RNA-target binding sequence that is complementary to an RNA target and an intramolecular reconfiguration sequence, wherein said intramolecular reconfiguration sequence comprises a tRNA aptamer scaffold comprising an inactive aptamer and a tRNA scaffold, and wherein said probe is configured such that binding of said RNA target by said RNA-target binding sequence triggers said intramolecular reconfiguration sequence to form a tRNA-stabilized active aptamer such that an optically detectable output is generated by said active aptamer.

2. The probe of claim 1, wherein said intramolecular reconfiguration sequence comprises a Broccoli aptamer.

3. The probe of claim 1, wherein said optically detectable output generated by said active aptamer is a fluorescence signal.

4. The probe of claim 1, wherein, in the absence of the RNA target, a portion of the probe forms a hairpin comprising a stem and a loop, and wherein the RNA-target binding sequence comprising a first portion that is located in the loop and a second portion that is located in the stem.

5. The probe of claim 1, wherein, in the absence of the RNA target, a portion of the probe forms two hairpins: a 5' hairpin located the 5' end of the probe and a middle hairpin located in the middle of the probe; wherein each of the 5' hairpin and the middle hairpin comprises a stem, a loop, and a toehold domain comprising a 5' portion that is single-stranded and a 3' portion that forms a portion of the stem; and wherein the RNA-target binding sequence is located in the 5' hairpin toehold domain.

6. The probe of claim 1, wherein the tRNA scaffold of said probe is processed as a cellular tRNA, thereby increasing the RNA stability and resistance to nuclease degradation of the probe.

7. A method for imaging RNA in a live cell, the method comprising:
introducing the probe of claim 1 into said live cell; and
detecting the optically detectable output if said RNA target is present in said live cell.

8. The method of claim 7, wherein said RNA target comprises a single RNA molecule within a single live cell.

9. The probe of claim 4, wherein the stem comprises a portion of the tRNA aptamer scaffold, such that the tRNA aptamer scaffold cannot fold into its active form in the absence of the RNA target; and
wherein binding of the RNA target to the RNA-target binding sequence disrupts the hairpin structure, allowing the tRNA aptamer scaffold to fold into its active form.

10. The probe of claim 4, wherein the loop is approximately 15 to 24 nucleotides in length.

11. The probe of claim 5, wherein the middle hairpin stem comprises a portion of the tRNA aptamer scaffold, such that the tRNA aptamer scaffold cannot fold into its active form in the absence of the RNA target; and
wherein binding of the RNA target to the RNA-target binding sequence disrupts the 5' hairpin structure, allowing a portion of the 5' hairpin loop to bind to the middle hairpin toehold, thereby disrupting the middle hairpin structure and allowing the tRNA aptamer scaffold to fold into its active form.

12. The probe of claim 1, wherein, in the absence of the RNA target, a portion of the probe forms two hairpins: a 3' hairpin located the 3' end of the probe and a middle hairpin located in the middle of the probe; wherein each of the 3' hairpin and the middle hairpin comprises a stem, a loop, and a toehold domain comprising a 3' portion that is single-stranded and a 5' portion that is forms a portion of the stem;

and wherein the RNA-target binding sequence is located in the 3' hairpin toehold domain.

13. The probe of claim 12, wherein the middle hairpin stem comprises a portion of the tRNA aptamer scaffold, such that the tRNA aptamer scaffold cannot fold into its active form in the absence of the RNA target; and wherein binding of the RNA target to the RNA-target binding sequence disrupts the 3' hairpin structure, allowing a portion of the 3' hairpin loop to bind to the middle hairpin toehold, thereby disrupting the middle hairpin structure and allowing the tRNA aptamer scaffold to fold into its active form.

14. The probe of claim 1, wherein the optically detectable output is produced by the binding of the active aptamer to a conditionally fluorescent dye molecule.

15. The probe of claim 14, wherein the aptamer is Broccoli and the conditionally fluorescent dye molecule is DFHBI-1T.

* * * * *

SEQUENCE LISTING

<160> NUMBER OF SEQ ID NOS: 8

<210> SEQ ID NO 1
<211> LENGTH: 178
<212> TYPE: RNA
<213> ORGANISM: Artificial Sequence
<220> FEATURE:
<223> OTHER INFORMATION: synthetic

<400> SEQUENCE: 1
cgaccaucuc cacuuauccg gaaguuucau cuuaaagucc uuguaacagu cgucaagacg      60
aaacgcccgg auagcucagu cgguagagca gcggagacgg ucggguccag auauucguau    120 cgucgaguagagugugggc uccgcgggucagggggcaagucccuguuc gggcgcca          178

<210> SEQ ID NO 2
<211> LENGTH: 31
<212> TYPE: RNA
<213> ORGANISM: Artificial Sequence
<220> FEATURE:
<223> OTHER INFORMATION: synthetic

<400> SEQUENCE: 2
gacgacuguu acaaggacuu aagaugaaa c                                     31

<210> SEQ ID NO 3
<211> LENGTH: 166
<212> TYPE: RNA
<213> ORGANISM: Artificial Sequence
<220> FEATURE:
<223> OTHER INFORMATION: synthetic

<400> SEQUENCE: 3
cuuauccggg aguuucaucu uaaaguccuu guaacagucg ucaagacgaa acgcccggau      60
agcucagucg guagagcagc ggagacgguc ggguccagau auucguaucu gucgaguaga    120
gugugggcuc cgcgggucca ggguucaagu cccuguucgg gcgcca                   166

<210> SEQ ID NO 4
<211> LENGTH: 31
<212> TYPE: RNA
<213> ORGANISM: Artificial Sequence
<220> FEATURE:
<223> OTHER INFORMATION: synthetic

<400> SEQUENCE: 4
gacgacuguu acaaggacuu aagaugaaa c                                     31

<210> SEQ ID NO 5
<211> LENGTH: 175
<212> TYPE: RNA
<213> ORGANISM: Artificial Sequence
<220> FEATURE:
<223> OTHER INFORMATION: synthetic

<400> SEQUENCE: 5
ccguauccga uuauccggaa guuucaucuu aaaguccuug uaacagucgu caagacgaaa      60
cgcccggaua gcucagucgg uagagcagcg gagacggucg gguccagaua uucguaucug    120
ucgaguagag gugugggcucc gcggguccag gguucaaguc ccuguucggg cgcca         175

<210> SEQ ID NO 6
<211> LENGTH: 31
<212> TYPE: RNA
<213> ORGANISM: Artificial Sequence

```
<220> FEATURE:
<223> OTHER INFORMATION: synthetic

<400> SEQUENCE: 6
gacgacuguu acaaggacuu aagaugaaa c                                31

<210> SEQ ID NO 7
<211> LENGTH: 175
<212> TYPE: RNA
<213> ORGANISM: Artificial Sequence
<220> FEATURE:
<223> OTHER INFORMATION: synthetic

<400> SEQUENCE: 7
ccguauccga uuauccggaa guuuccguau ucugugaagc ccuaggaucc gauacagaaa    60
cgcccggaua gcucagucgg uagagcagcg gagacggucg gguccagaua uucguaucug   120
ucgaguagag ugugggcucc gcggguccag gguucaaguc ccuguucggg cgcca        175

<210> SEQ ID NO 8
<211> LENGTH: 31
<212> TYPE: RNA
<213> ORGANISM: Artificial Sequence
<220> FEATURE:
<223> OTHER INFORMATION: synthetic

<400> SEQUENCE: 8
cggacccuag ggcuucacag aauacggaaa c                                31
```